US005998657A

United States Patent [19]
Gogate et al.

[11] Patent Number: 5,998,657
[45] Date of Patent: Dec. 7, 1999

[54] PROCESS FOR THE GENERATION OF α, β-UNSATURATED CARBOXYLIC ACIDS AND ESTERS USING NIOBIUM CATALYST

[75] Inventors: Makarand Ratnakav Gogate, Durham; James Jerome Spivey, Cary, both of N.C.; Joseph Robert Zoeller, Kingsport, Tenn.

[73] Assignee: Eastman Chemical Company, Kingsport, Tenn.

[21] Appl. No.: 09/060,468

[22] Filed: Apr. 15, 1998

[51] Int. Cl.$^6$ .............................. C07C 69/52; C07B 35/00
[52] U.S. Cl. ............................................. 560/205; 562/599
[58] Field of Search .............................. 560/205; 562/599

[56] References Cited

U.S. PATENT DOCUMENTS

| | | |
|---|---|---|
| 3,466,320 | 9/1969 | Hargis . |
| 4,336,403 | 6/1982 | Merger et al. . |
| 4,743,706 | 5/1988 | Guttmann et al. . |

FOREIGN PATENT DOCUMENTS

| | | |
|---|---|---|
| 0138295 | 4/1985 | European Pat. Off. . |
| 1207415 | 9/1970 | United Kingdom . |

OTHER PUBLICATIONS

U.S. application No. 08/775,935, Gogate et al., filed Jan. 3, 1997.
Mamoru AI, "Vapor–Phase Aldol Condensation of Formaldehyde with Acetic Acid on $V_2O_5$–$P_2O_5$ Catalysts", *Journal of Catalysis 107*, pp. 201–208 (1987).
"The Production of Methacrylic Acid by the Vapor–Phase Aldol Condensation of Propionic Acid with Formaldehyde", *Journal of Catalysis 124*, pp. 293–296 (1990).
Mamoru AI, "Vapor–Phase Aldol Condensation of Formaldehyde with Propionic Acid on Vanadium Pentoxide–Phosphorus Pentoxide", *Applied Catalysis*, 36, pp. 221–230 (1988).
Mamoru AI, "The Effects of the Reaction Variables on the Yields of Acrylic Acid and Methyl Acrylate in the Reaction of Acetic Acid with Methanol in the Presence of Oxygen", *Bulletin of the Chemical Society of Japan*, 63, pp. 199–202 (1990).
Mamoru AI, "Reaction of Propionic Acid with Methylal Over Vanadium–Silicon–Phosphorus Oxide", *Applied Catalysis*, 63, pp. 365–373 (1990).
Mamoru Al, "Reaction of Methyl Propionate with Methylal over V–Si–P Ternary Oxide Catalysts", *Bulletin of the Chemical Society of Japan*, 63, pp. 3722–3724 (1990).
Mamoru Al, "The Production of Methacrylic Acid by the Vapor–Phase Aldol Condensation over V–Si–P Ternary Oxide Catalyst", *Bulletin of the Chemical Society of Japan*, 63, pp. 1217–1220 (1990).
Mamoru Al, "Effect of the Composition of Vanadium–Titanium Binary Phosphate on Catalytic Performance in Vapor–Phase Aldol Condensation", *Applied Catalysis*, 54, pp. 29–36 (1989).
Mamoru Al, "Reaction of Acetic Acid with Methanol over Vanadium–Titanium Binary Phosphate Catalysts in the Presence of Oxygen", *Applied Catalysis*, 59, pp. 227–235 (1990).
M. Al, "Preparation of High–Surface–Area Titanium–Vanadium Binary Pyrophosphate Catalysts", *Applied Catalysis*, 48, pp. 51–61 (1989).
Wataru Ueda et al., "Coupling Reaction Between Methylpropionate and Methanol to Form Methylmethacylate Over Metal Ion–Contained Magnesium Oxide Catalysts", *Chemistry Letters; The Chemical Society of Japan*, pp. 810–820 (1985).

*Primary Examiner*—Gary Geist
*Assistant Examiner*—Robert W. Deemie

[57] ABSTRACT

A process using a niobium catalyst includes the step of reacting an ester or carboxylic acid with oxygen and an alcohol in the presence a niobium catalyst to respectively produce an α,β-unsaturated ester or carboxylic acid. Methanol may be used as the alcohol, and the ester or carboxylic acid may be passed over the niobium catalyst in a vapor stream containing oxygen and methanol. Alternatively, the process using a niobium catalyst may involve the step of reacting an ester and oxygen in the presence the niobium catalyst to produce an α,β-unsaturated carboxylic acid. In this case the ester may be a methyl ester. In either case, niobium oxide may be used as the niobium catalyst with the niobium oxide being present on a support. The support may be an oxide selected from the group consisting of silicon oxide, aluminum oxide, titanium oxide and mixtures thereof. The catalyst may be formed by reacting niobium fluoride with the oxide serving as the support. The niobium catalyst may contain elemental niobium within the range of 1 wt % to 70 wt %, and more preferably within the range of 10 wt % to 30 wt %. The process may be operated at a temperature from 150 to 450° C. and preferably from 250 to 350° C. The process may be operated at a pressure from 0.1 to 15 atm. absolute and preferably from 0.5–5 atm. absolute. The flow rate of reactants may be from 10 to 10,000 L/$kg_{(cat)}$/h, and preferably from 100 to 1,000 L/$kg_{(cat)}$/h.

39 Claims, No Drawings

PROCESS FOR THE GENERATION OF α, β-UNSATURATED CARBOXYLIC ACIDS AND ESTERS USING NIOBIUM CATALYST

GOVERNMENT LICENSE RIGHTS

This invention was made with Government support under Contract NO. DE-AC22-94PC94065 awarded by the Department of Energy. The Government has certain rights in this invention.

BACKGROUND OF THE INVENTION

1. Field of the Invention

The present invention relates in general to catalytic generation of α,β-unsaturated carboxylic acids and esters, and more particularly to preparing α,β-unsaturated carboxylic acids and esters from carboxylic acids and esters using a niobium catalyst.

2. Description of the Related Art

α,β-Unsaturated acids, particularly acrylic acid (AA), methacrylic acid (MAA), and their esters, are useful organic compounds whose polymeric forms find a myriad of applications, including plastic sheeting for signs, coatings (including latex paints), adhesives, fibers, and synthetic resins. Currently, MAA and methyl methacrylate (MMA) are manufactured industrially primarily by the acetone cyanohydrin process, which uses toxic hydrogen cyanide and generates large quantities of ammonium bisulfate wastes, which have to be disposed or regenerated at substantial cost. Acrylic acid is generally manufactured by a two step oxidation of propylene.

For nearly a quarter of a century, there has been a desire in the industry to replace the current acetone cyanohydrin process for methacrylic acid with a process that eliminates both the environmentally deleterious ammonium bisulfate waste and the safety hazards associated with handling very toxic hydrogen cyanide. Further, both the acrylic acid and methacrylic acid processes are currently dependent upon petrochemical feedstocks. Over the long term, there is a desire to diversify the chemical industry's feedstock options, particularly using synthesis gas, which can be generated from more abundant natural gas, coal, and heavy oil based carbon sources. One process, which has been envisioned as a means for attaining these goals, is shown generically in reaction [1] below.

$$R^1CH_2CO_2H + R^2CHO \leftrightarrow R^2HC=C(R^1)CO_2H + H_2O \quad [1]$$

In the condensation of formaldehyde with acetic acid to generate acrylic acid, $R^1$ and $R^2$ are hydrogen atoms. In the condensation of formaldehyde with propionic acid to generate methacrylic acid, R is a methyl group and $R^2$ is a hydrogen atom. To understand reaction [1] and the subsequent reactions, it is important to note that the carbon atom ($R^2\underline{C}HO$) shown in the reactant aldehyde forms a double bond with the α-carbon in the reactant acid. The α-carbon in the reactant acid is the carbon atom ($R^1\underline{C}H_2CO_2H$) adjacent to the acid carbon. $R^1$ is bonded to the α-carbon in both the reactant acid and the product acid. However, due to the spatial relationship of the product, $R^1$ is shown in the middle of the product, whereas $R^2$ is shown to the left.

One drawback to these prior processes has been the need to generate or import difficult to handle formaldehyde. It would be advantageous if the formaldehyde could be replaced with methanol, which is more easily handled. Unfortunately, when methanol has been successfully used to form carbon-carbon bonds, the products are generally simple alkylation products via reaction [2]. The more desired reaction, is reaction [3]:

$$R^3CH_2CO_2R^4 + R^5CH_2OH \leftrightarrow R^5CH_2(R^3)CO_2R^4 + H_2O \quad [2]$$

$$R^6CH_2CO_2R^7 + R^8CH_2OH + O_2 \leftrightarrow R^8HC=C(R^6)CO_2R^7 + 2H_2O \quad [3]$$

where $R^3$ through $R^8$ are independently a hydrogen atom, a methyl or other alkyl group, or another organic.

Reaction [3] has been accomplished in only very few select cases, entailing the use of a mixture of methanol and oxygen in the presence of catalysts consisting of vanadium and phosphorous. That is, vanadium-phosphorous oxides are used to catalyze the reaction. The use of a phosphorous component is neither simple nor desired. Furthermore, vanadium oxide ($V_2O_5$), although extensively used in the industry as a catalyst, is a toxic substance with a myriad of deleterious effects. As such, it is strictly controlled in the environment and work place.

The inventors of the present application developed a condensation reaction of carboxylic acid derivatives with formaldehyde over supported niobium catalysts. However, this development does not contemplate the use of methanol and oxygen as an alternative to formaldehyde. Further, there is no prior art indicating that niobium will effect an oxidation of methanol to formaldehyde, which is an intrinsic requirement for this reaction to proceed.

SUMMARY OF THE INVENTION

Accordingly, it is an object of the present invention to provide a process for producing α,β-unsaturated carboxylic acids and esters which does not employ toxic hydrogen cyanide and which does not require costly disposal or regeneration of ammonium bisulfate.

It is a further object of the present invention to provide a process for producing α,β-unsaturated carboxylic acids and esters which does not require generation and transportation of difficult to handle formaldehyde.

It is another object of the present invention to provide a process for producing α,β-unsaturated carboxylic acids and esters which does not require phosphorous or toxic vanadium oxide.

These and other objects are accomplished by providing a process using a niobium catalyst which includes the step of reacting an ester or carboxylic acid with oxygen and an alcohol in the presence a niobium catalyst to respectively produce an α,β-unsaturated ester or carboxylic acid. Methanol may be used as the alcohol, and the ester or carboxylic acid may be passed over the niobium catalyst in a vapor stream containing oxygen and methanol. The reaction of the ester or carboxylic acid with oxygen and the alcohol may proceed according to reaction [3]

$$R^6CH_2CO_2R^7 + R^8CH_2OH + \tfrac{1}{2}O_2 \leftrightarrow R^8HC=C(R^6)CO_2R^7 + 2H_2O \quad [3].$$

where $R^6$ is selected from the group consisting of a hydrogen atom, an alkyl group, an aryl group, an aralkyl group, a cycloalkyl group and an alkylaryl group. $R^6$ is preferably a methyl group. $R^8$ is selected from the group consisting of a hydrogen atom, an alkyl group, an aryl group and an olefinic group.

Alternatively, the process using a niobium catalyst may involve the step of reacting an ester and oxygen in the presence the niobium catalyst to produce an α,β-unsaturated carboxylic acid. In this case the ester may be a methyl ester and the reaction of the ester with oxygen may be according to reaction [4]

$$R^9CH_2CO_2CH_2R^{10} + \tfrac{1}{2} O_2 \longleftrightarrow R^{10}HC=C(R^9)CO_2H + H_2O \qquad [4]$$

where $R^9$ is selected from the group consisting of a hydrogen atom, an alkyl group, an aryl group, an aralkyl group, a cycloalkyl group and an alkylaryl group, and $R^{10}$ is a methyl group.

In either case, niobium oxide may be used as the niobium catalyst with the niobium oxide being present on a support. The support may be an oxide selected from the group consisting of silicon oxide, aluminum oxide, titanium oxide and mixtures thereof. The catalyst may be formed by reacting niobium fluoride with the oxide serving as the support. The niobium catalyst may contain elemental niobium within the range of 1 wt % to 70 wt %, and more preferably within the range of 10 wt % to 30 wt %.

The process may be operated at a temperature from 150 to 450° C. and preferably from 250 to 350° C. The process may be operated at a pressure from 0.1 to 15 atm. absolute and preferably from 0.5–5 atm. absolute. The flow rate of reactants may be from 10 to 10,000 $L/kg_{(cat)}/h$, and preferably from 100 to 1,000 $L/kg_{(cat)}/h$.

DETAILED DESCRIPTION OF THE PREFERRED EMBODIMENTS

The invention will now be described in detail with reference to preferred embodiments given by way of example only, and not limitation.

The present invention produces α,β-unsaturated carboxylic acids and esters using a niobium catalyst, which is much safer than several of the previously employed catalysts. Niobium (V) oxide, $Nb_2O_5$, may be used to form the desired products. Pure niobium oxide will work to produce the products. However, the reaction may also use niobium oxide in the presence of a support, which can be selected from any number of oxides of silicon, aluminum, titanium, or mixtures thereof. There may be certain benefits associated with the use of a support, such as more highly dispersed niobium, improved rates, and larger sized catalyst particles. The larger size is particularly important since the particle sizes generally available for pure niobium oxide are small, which makes them difficult to use in heterogeneous vapor phase processes (described below).

The niobium may be incorporated into the support using any of the variety of coprecipitation and impregnation techniques known in the art, and the niobium source may be any of the available compounds of niobium. However, it has been found to be particularly convenient to add the niobium component to the support by using one of the commercially available niobium fluorides since these are the least moisture sensitive of the commonly available niobium sources and provide well dispersed catalysts.

The niobium content of the catalyst can vary widely. At the high end, pure niobium (V) oxide can be applied. This would represent a level of 70 wt. % of elemental niobium. However, we have found it to be quite advantageous to use supports. At the lower end, niobium content can be as low as 1 wt. %, but the best performance is likely to be obtained with catalysts containing 10–30 wt. % niobium.

1. First Embodiment

The niobium catalyst can be used to produce α,β-unsaturated acids, particularly acrylic acid (AA), methacrylic acid (MAA), and their methyl esters. These products can be generated from methanol and a carboxylic acid (or methyl ester), from reaction [3]. The alcohol forms an aldehyde intermediate, which in turn reacts in a manner similar to reaction [1]. One way to do this is by passing a vapor stream containing oxygen, the carboxylic acid derivative, and methanol over a simpler and potentially less toxic niobium based catalyst.

$$R^6CH_2CO_2R^7 + R^8CH_2OH + \tfrac{1}{2} O_2 \longleftrightarrow R^8HC=C(R^6)CO_2R^7 + 2H_2O \qquad [3]$$

In reaction [3], the carboxylic acid or ester reactant may have $R^6$ chosen from a hydrogen atom and wide variety of available organics, including alkyl groups, aryl groups, aralkyl groups, cycloalkyl groups and alkylaryl groups. In addition, olefinic groups may also be used. When $R^6$ is aryl, there may be up to 10 carbons in the aryl/aralkyl group. In the case where $R^6$ is an olefinic or alkyl chain, the chain length may consist of up to 21 carbons. However, this invention may be more practical when using acids and ester with shorter chain lengths, generally with up to 15 carbons, as these materials are more easily removed from the catalyst. In the most preferred cases, $R^6$ is hydrogen or a methyl group. However, this is not based on any anticipated higher performance for these feedstocks, but instead on the fact that the products from these materials, acrylic acid and methacrylic acid respectively, possess the largest available commercial market for the product derived from this process.

$R^7$ is either hydrogen or a methyl group or other organic. One can certainly anticipate the use of higher esters, but these may lead to deleterious by-products resulting from the oxidation of the longer chain ester moiety. Therefore, perhaps the use of esters longer than a methyl ester is less desirable.

If methanol is used as the alcohol, the source methanol is unimportant in the process. Certainly other alcohols can be used. $R^8$ may be a hydrogen atom, an alkyl, aryl, aralkyl, cycloalkyl, or alkylaryl group.

2. Second Embodiment

As an alternative to reaction [3], α,β-unsaturated acids can be produced by reacting an ester with oxygen in the presence of a niobium catalyst, without requiring any alcohol. Methyl esters are particularly suitable. This reaction proceeds according to reaction [4]

$$R^9CH_2CO_2CH_2R^{10} + \tfrac{1}{2} O_2 \longleftrightarrow R^{10}HC=C(R^9)CO_2H + H_2O \qquad [4]$$

In reaction [4] $R^9$ may be chosen from the same elements and compounds from which $R^6$ is chosen for reaction [3]. $R^{10}$ is a methyl group or other organic.

Reaction [4] is actually a linear combination of three separate reactions. The first of these reactions is the reverse esterification of an ester (methyl propionate, for example) according to reaction [4a]

$$R^9CH_2CO_2CH_2R^{10} + H_2O \longleftrightarrow R^9CH_2CO_2H + R^{10}CH_2OH \qquad [4a]$$

The second of these reactions is the partial oxidation of an alcohol (methanol, for example) with oxygen according to reaction [4b]

$$R^{10}CH_2OH + \tfrac{1}{2} O_2 \longleftrightarrow R^{10}CHO + H_2O \qquad [4b]$$

The third of these reactions is the condensation of a carboxylic acid (propionic acid, for example) formed in reaction [4a] with the partially oxidized product (HCHO, for example) of reaction [4b], according to reaction [4c]

$$R^9CH_2CO_2H + R^{10}CHO \longleftrightarrow R^{10}HC=C(R^9)CO_2H + H_2O \qquad [4c]$$

It should be apparent that the ester provides an in situ source of the requisite alcohol. Although it may be easier in most cases to simply use an alcohol (perhaps methanol) and a carboxylic acid or ester according to the first embodiment. However, this second embodiment would be particularly useful when the ester (perhaps methyl ester) is more readily available. For instance, methyl acetate is generated as a by-product in the methanolysis of polyvinyl acetate to polyvinyl alcohol and long chain methyl esters are generated in the methanolysis of triglycerides.

For both the first and second embodiments, the reaction must be conducted in the presence of an oxygen containing gas. The oxygen can be added as pure oxygen, but it is more convenient (and typical) to use ordinary air. The oxygen may be further diluted with additional nitrogen or any other inert gas, such as helium or argon if desired. The key restriction is that the oxygen level must be maintained below the explosion limits of the mixture of carboxylic acid or ester, and methanol (if used) for safe operation. The explosion limits must be determined for each specific mixture.

The catalyst of this invention is subject to deactivation and steam may be used to help maintain catalyst activity in the process. However, although it is not necessary for the reaction, steam may also provide a means of promoting the direct conversion of methyl esters to the corresponding $\alpha,\beta$-unsaturated acid via reaction [4].

Whether steam is added or not, the catalyst eventually requires reactivation. This is readily accomplished by heating the catalyst in a stream of air at elevated temperatures, generally in the range of 350–500° C.

The process is generally conducted in the vapor phase. Therefore, useful temperatures and pressures in the reaction are somewhat dependent upon the catalyst substrate since the vapor pressure of the starting materials and products dictate the operable combinations of pressure and temperature. From a practical standpoint, the process may be operated from 150–450° C., with the preferred range being 250–350° C. and pressures can range from 0.1–15 atm. absolute, with the preferred range being 0.5–5 atm. absolute.

Flow rates of reactants through the process can vary widely and are a matter of empirical optimization for each catalyst and feed combination. However, it appears that flow rates within the range of from 10 to 10,000 L/kg$_{(cat)}$/h are useful. Flow rates within the range of from 100 to 1,000 L/kg$_{(cat)}$/h may be particularly useful.

EXAMPLES

Example 1

An Nb on silica catalyst used in this reaction were prepared by slowly adding 12.07 g of NbF$_5$ to 42.03 g of a silica (SiO$_2$) solution (36 percent silica in H$_2$O, Nalco colloidal silica) with stirring. After the addition was complete, the mixture was gradually heated, with stirring, to drive off water. The resultant mixture was calcined at 300° C. for 4 hours and then at 450° C. for 6 hours. The calcined material was then crushed and screen filtered to obtain a portion with a 16 to 25 mesh size (0.707 to 1.19 mm). This 16 to 25 mesh fraction was then used as the catalytic component in assembling the reactor described below.

The reactor was constructed using a ½ in.×16 in. (1.25 cm×40.6 cm) 316 stainless steel (SS) tube to serve as a preheater and a ½ in.×14 in. (1.25 cm×35.6 cm) 316 SS tube to serve as the reactor. The preheater was filled with quartz beads. The reactor tube was charged with 5 g of the catalyst whose preparation is described above. To hold the catalyst charge in the center of the reactor tube, quartz beads were used to fill the void volumes, and quartz wool was used to hold the catalyst and quartz beads in place. The preheater and reactor tube were aligned horizontally, connected by short (well-insulated) SS tubing, and each section was placed in a separate Lindberg furnace. A thermocouple was located in the reactor section at the same location as the catalyst bed. A nitrogen feed line and a liquid feed line were connected to the inlet of the preheater. The exit port of the reactor was connected to a condenser, and liquid product samples were collected after condensation. The gas outlet of the reactor system was connected to an outlet and an on-line gas chromatography (GC) device.

The reactor was operated by heating the preheater to 300° C. and introducing a continuous nitrogen diluent of 174 mmol/h through the system with the pressure maintained at about 2 atm. The reactor tube was then heated to 300° C. using the thermocouple in the reactor section to establish and maintain the temperature throughout the reaction. Upon reaching the desired temperature, a liquid feed of propionic acid and methanol were introduced to the preheater at a rate of 65 mmol/h for each component. Oxygen was also fed to the reactor at a rate of 46 mmol/h (excess oxygen). Each reaction was run for a period of 2.58 h.

The preheater temperature of 300° C. was sufficient to vaporize both the methanol and the propionic acid. The vaporized components were directed through the reactor tube by the nitrogen diluent. After passage through the reactor tube, the liquid components were condensed, weighed, and analyzed by GC for diethyl ketone, PA, MP, MAA, and MMA. The gaseous effluent was periodically analyzed for CO and CO$_2$. For gas analysis, a fixed-volume loop injection onto a molecular sieve (5 Angstroms) and a column isolation sequence in conjunction with a thermal conductivity detector (TCD) were used. For liquid analysis, a fused silica capillary column with a 1-mm film thickness of silica covering was used, with a flame ionization detector (FID).

Using this method, methacrylic acid and methyl methacrylate were coproduced at a rate of 75.3 g/kg$_{(cat)}$-h (0.88 mol/kg$_{(cat)}$-h) and 69.8 g/kg$_{(cat)}$-h (0.70 mol/kg$_{(cat)}$-h), respectively. The total production rate of methacrylates (methacrylic acid+methyl methacrylate) was 1.58 mol/kg$_{(cat)}$-h.

Example 2

The process in Example 1 was repeated except that the propionic acid and methanol were replaced with methyl propionate and steam. Using this method, methacrylic acid and methyl methacrylate were coproduced at a rate of 44.7 g/kg$_{(cat)}$-h (0.52 mol/kg$_{(cat)}$-h) and 27.0 g/kg$_{(cat)}$-h (0.27 mol/kg$_{(cat)}$-h), respectively. The total production rate of methacrylates (methacrylic acid+methyl methacrylate) was 0.79 mol/kg$_{(cat)}$-h. This demonstrated the conversion of esters directly to the $\alpha,\beta$-unsaturated acid or its methyl ester.

The invention has been described in detail with particular reference to preferred embodiments thereof and examples, but it will be understood that variations and modifications can be effected within the spirit and scope of the invention.

We claim:

1. A process using a niobium catalyst, comprising the step of reacting an ester or carboxylic acid with oxygen and an alcohol in the presence a niobium catalyst, and in the substantial absence of vanadium and phosphorous, to respectively produce an $\alpha,\beta$-unsaturated ester or carboxylic acid.

2. A process using a niobium catalyst according to claim 1, wherein
methanol is used as the alcohol, and
the ester or carboxylic acid is passed over the niobium catalyst in a vapor stream containing oxygen and methanol.

3. A process using a niobium catalyst according to claim 1, wherein the reaction of the ester or carboxylic acid with oxygen and the alcohol is according to reaction [3]

$$R^6CH_2CO_2R^7 + R^8CH_2OH + \tfrac{1}{2} O_2 \longleftrightarrow R^8HC=C(R^6)CO_2R^7 + 2\ H_2O \quad [3]$$

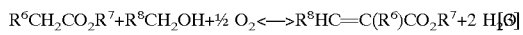

where $R^6$ through $R^8$ are independently an organic group or a hydrogen atom.

4. A process using a niobium catalyst according to claim 3, wherein $R^8$ is selected from the group consisting of a hydrogen atom, an alkyl group, an aryl group and an olefinic group.

5. A process using a niobium catalyst according to claim 3, wherein $R^6$ is selected from the group consisting of a hydrogen atom, an alkyl group, an aryl group, an aralkyl group, a cycloalkyl group and a alkylaryl group.

6. A process using a niobium catalyst according to claim 3, wherein $R^6$ is an olefinic or alkyl chain having a chain length up to 21 carbon atoms long.

7. A process using a niobium catalyst according to claim 1, wherein the carboxylic acid or ester reactant has a chain length up to 15 carbon atoms long.

8. A process using a niobium catalyst according to claim 3, wherein $R^6$ is a methyl group.

9. A process using a niobium catalyst according to claim 1, wherein niobium oxide is used as the niobium catalyst.

10. A process using a niobium catalyst according to claim 1, wherein a niobium oxide on a support is used as the catalyst.

11. A process using a niobium catalyst according to claim 1, wherein the support is an oxide selected from the group consisting of silicon oxide, aluminum oxide, titanium oxide and mixtures thereof.

12. A process using a niobium catalyst according to claim 1, wherein the catalyst is formed by reacting niobium fluoride with an oxide selected from the group consisting of silicon oxide, aluminum oxide, titanium oxide, and mixtures thereof.

13. A process using a niobium catalyst according to claim 1, wherein the niobium catalyst contains elemental niobium within the range of 1 wt % to 70 wt %.

14. A process using a niobium catalyst according to claim 1, wherein wherein the niobium catalyst contains elemental niobium within the range of 10 wt % to 30 wt %.

15. A process using a niobium catalyst, comprising the step of reacting an ester and oxygen in the presence a niobium catalyst, and in the substantial absence of vanadium and phosphorous, to produce an α,β-unsaturated carboxylic acid.

16. A process using a niobium catalyst according to claim 15, wherein a methyl ester is reacted with oxygen.

17. A process using a niobium catalyst according to claim 15, wherein the reaction of the ester with oxygen is according to reaction [4]

$$R^9CH_2CO_2CH_2R^{10} + \tfrac{1}{2} O_2 \longleftrightarrow R^{10}HC=C(R^9)CO_2H + H_2O \quad [4]$$

where $R^9$ is a hydrogen or an organic group and $R^{10}$ is an organic group.

18. A process using a niobium catalyst according to claim 17, wherein $R^9$ is selected from the group consisting of a hydrogen atom, an alkyl group, an aryl group and an olefinic group and $R^{10}$ is a methyl group.

19. A process using a niobium catalyst according to claim 15, wherein niobium oxide is used as the niobium catalyst.

20. A process using a niobium catalyst according to claim 15, wherein a niobium oxide on a support is used as the catalyst.

21. A process using a niobium catalyst according to claim 15, wherein the support is an oxide selected from the group consisting of silicon oxide, aluminum oxide, titanium oxide and mixtures thereof.

22. A process using a niobium catalyst according to claim 15, wherein the catalyst is formed by reacting niobium fluoride with an oxide selected from the group consisting of silicon oxide, aluminum oxide, titanium oxide, and mixtures thereof.

23. A process using a niobium catalyst according to claim 15, wherein the niobium catalyst contains elemental niobium within the range of 1 wt % to 70 wt %.

24. A process using a niobium catalyst according to claim 15, wherein the niobium catalyst contains elemental niobium within the range of 10 wt % to 30 wt %.

25. A process using a niobium catalyst according to claim 1, wherein the process is operated at a temperature from 150 to 450° C.

26. A process using a niobium catalyst according to claim 15, wherein the process is operated at a temperature from 150 to 450° C.

27. A process using a niobium catalyst according to claim 1, wherein the process is operated at a temperature from 250 to 350° C.

28. A process using a niobium catalyst according to claim 15, wherein the process is operated at a temperature from 250 to 350° C.

29. A process using a niobium catalyst according to claim 1, wherein the process is operated at a pressure from 0.1 to 15 atm. absolute.

30. A process using a niobium catalyst according to claim 15, wherein the process is operated at a pressure from 0.1 to 15 atm. absolute.

31. A process using a niobium catalyst according to claim 1, wherein the process is operated at a pressure from 0.5–5 atm. absolute.

32. A process using a niobium catalyst according to claim 15, wherein the process is operated at a pressure from 0.5–5 atm. absolute.

33. A process using a niobium catalyst according to claim 1, wherein the process is operated at a flow rate of reactants of from 10 to 10,000 L/$kg_{(cat)}$/h.

34. A process using a niobium catalyst according to claim 15, wherein the process is operated at a flow rate of reactants of from 10 to 10,000 L/$kg_{(cat)}$/h.

35. A process using a niobium catalyst according to claim 1, wherein the process is operated at a flow rate of reactants of from 100 to 1,000 L/$kg_{(cat)}$/h.

36. A process using a niobium catalyst according to claim 15, wherein the process is operated at a flow rate of reactants of from 100 to 1,000 L/$kg_{(cat)}$/h.

37. A process using a niobium catalyst according to claim 15, wherein the ester is passed over the niobium catalyst in a vapor stream containing oxygen.

38. A process using a niobium catalyst according to claim 1, wherein a vapor stream of reactants diluted with an inert gas is passed over the niobium catalyst.

39. A process using a niobium catalyst according to claim 15, wherein a vapor stream of reactants diluted with an inert gas is passed over the niobium catalyst.

* * * * *

UNITED STATES PATENT AND TRADEMARK OFFICE
CERTIFICATE OF CORRECTION

PATENT NO.: 5,998,657
DATED : December 7, 1999
INVENTOR(S): Gogate et al

It is certified that [an/error[s]] appears in the above-identified patent and that said Letters Patent is hereby corrected as shown below:

Col. 7, line 11, change to
-- $R^6CH_2CO_2R^7 + R^8CH_2OH + \frac{1}{2}O_2 \rightarrow R^8HC=C(R^6)CO_2R^7 + 2H_2O$ [3]

Signed and Sealed this

Twenty-fourth Day of October, 2000

Attest:

Q. TODD DICKINSON

*Attesting Officer*  *Director of Patents and Trademarks*